United States Patent
Huai et al.

(10) Patent No.: US 11,297,294 B1
(45) Date of Patent: Apr. 5, 2022

(54) COLOR ENHANCEMENT OF ENDOSCOPIC IMAGE

(71) Applicant: Xiaoning Huai, Sunnyvale, CA (US)

(72) Inventors: Xiaoning Huai, Sunnyvale, CA (US); Liangxin Wu, Shenzhen (CN); Bo Xia, Shenzhen (CN); Shuxian Kan, Shenzhen (CN)

(73) Assignee: Shenzhen Jifu Technology Co, Ltd, Shenzhen (CN)

( * ) Notice: Subject to any disclaimer, the term of this patent is extended or adjusted under 35 U.S.C. 154(b) by 1 day.

(21) Appl. No.: 17/326,121

(22) Filed: May 20, 2021

(51) Int. Cl.
| | |
|---|---|
| *G06T 7/00* | (2017.01) |
| *H04N 9/64* | (2006.01) |
| *H04N 9/67* | (2006.01) |
| *G06T 5/40* | (2006.01) |
| *G06T 5/50* | (2006.01) |
| *G06T 7/80* | (2017.01) |
| *A61B 1/00* | (2006.01) |
| *G06T 7/90* | (2017.01) |

(52) U.S. Cl.
CPC ......... *H04N 9/646* (2013.01); *A61B 1/00009* (2013.01); *G06T 5/40* (2013.01); *G06T 5/50* (2013.01); *G06T 7/80* (2017.01); *G06T 7/90* (2017.01); *H04N 9/643* (2013.01); *H04N 9/67* (2013.01); *G06T 2207/10024* (2013.01); *G06T 2207/10068* (2013.01); *G06T 2207/30004* (2013.01)

(58) Field of Classification Search
CPC .......... H04N 9/646; H04N 9/67; H04N 9/643; H04N 9/0451; H04N 9/04521; H04N 9/647; H04N 2005/2255; G06T 7/80; G06T 7/90; G06T 7/0012; G06T 7/0014; G06T 7/74; G06T 7/62; G06T 5/50; G06T 5/40; G06T 5/007; G06T 5/00; G06T 5/001; G06T 5/005; G06T 2207/10024; G06T 2207/10068; G06T 2207/30004; G06T 2207/30096; G06T 2207/20172; G06T 2207/30028; G06T 2207/10016; G06T 2210/41; G06T 2219/2012; A61B 1/00009; A61B 1/0005; A61B 1/05; A61B 1/00; A61B 1/043; A61B 1/0669; A61B 1/0638; A61B 5/061; G06K 9/6215; G06K 9/4652; G06K 2209/051; Y10S 600/921; G02B 26/008

See application file for complete search history.

(56) References Cited

U.S. PATENT DOCUMENTS

| | | | | |
|---|---|---|---|---|
| 2005/0275736 | A1* | 12/2005 | Chiu .................... | H04N 9/646 348/272 |
| 2008/0088857 | A1* | 4/2008 | Zimmer .................. | H04N 1/56 358/1.6 |
| 2011/0310246 | A1* | 12/2011 | Hornabrook ......... | G06K 9/4661 348/142 |

(Continued)

*Primary Examiner* — Jose L Couso

(57) ABSTRACT

The invention provides an image color enhancement system, method, storage medium and endoscope. Based on that the human skin color and the basic tone of endoscopic image are similar, utilizing a standard data set of Macbeth color card, a color correction matrix for skin color enhancement is generated, which is used by an endoscope for real time image capture, resulting in a vivid expression of the basic tone of an endoscopic image without introducing artifacts in other tonal image parts.

3 Claims, 4 Drawing Sheets

(56) References Cited

U.S. PATENT DOCUMENTS

Figure 1:
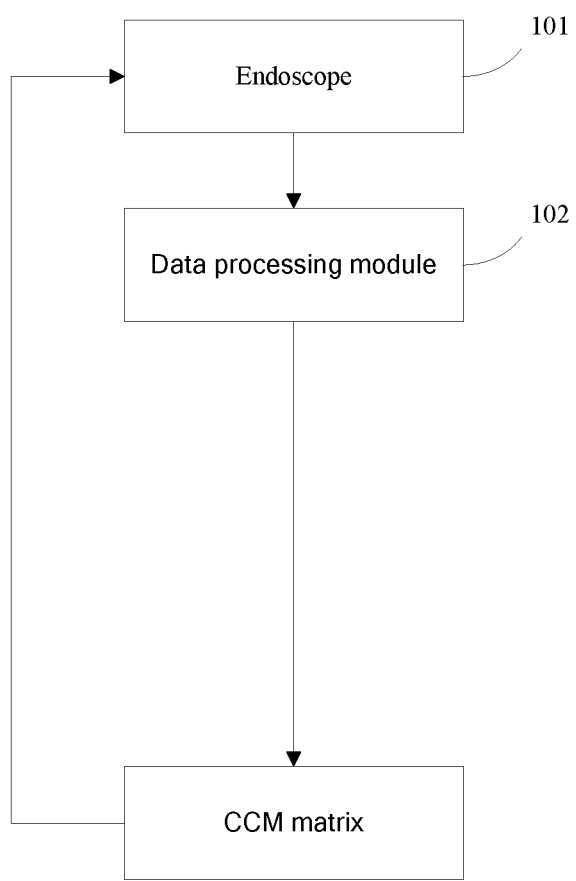

2014/0163319 A1\* 6/2014 Blanquart ............ A61B 1/0684
  600/109
2015/0348245 A1\* 12/2015 Horiuchi .................. H04N 9/67
  382/167
2019/0197712 A1\* 6/2019 Talbert ...................... G01J 3/10

\* cited by examiner

COLOR ENHANCEMENT OF ENDOSCOPIC IMAGE

TECHNICAL FIELD

The invention relates to the field of image processing, and in particular the field of an endoscopic image color enhancement system, method and storage medium.

BACKGROUND

A human eye cannot directly see the digestive tract in its native state. The image captured by an endoscope has different color effects due to the differences in devices and tuning methods by different manufacturers or end users. To date, there is no standard on image color rendering or enhancement in the endoscope industry. A generic image processor used in an endoscope provides adjustable hue and saturation options as a mean to enhance the image color to different flavors for different end users, which typically operates on the entire image by a set of same gains resulting in an expected enhanced color in some parts of an image and unexpected appearances or artifacts in some other parts of the image. As an example, a prominent endoscope provider Olympus of Japan has listed in its specifications of products the adjustable hue and saturation options.

SUMMARY OF THE INVENTION

To solve the above-mentioned limitation of the prior art, the present invention proposes an endoscopic image color enhancement system and method.

An endoscopic image color enhancement system, comprising:

An endoscope configured to: acquire a first image of the Macbeth color card under a standard light source matching a color temperature of the illumination of the endoscope, and adopt a color correction matrix generated based on the first image for skin tone enhancement to enhance color of endoscopic images; and A data processing module configured to:

acquire a set of color enhancement target data, the set of color enhancement target data including coordinates (H0, S0, V0) of a point P0 in HSV space;

obtain data of the color patch of the first row and the first column of the Macbeth color card, including the coordinates (H1, S1, V1) of a point P1 in HSV space;

obtain data of the color patches in the first row and second column of the Macbeth color card, including the coordinates (H2, S2, V2) of a point P2 in the HSV space;

perform a first interpolation of the coordinates of P0 and the coordinates of P1, then replace the coordinates of P1 with the result of the first interpolation, and perform a second interpolation of the coordinates of P0 and the coordinates of P2, and then use the result of the second interpolation to replace the coordinates of P2;

merge data of the rest patches of Macbeth color card color with the replaced P1 coordinates and the replaced P2 coordinates resulting in a data set of the Macbeth color card for skin tone enhancement;

generate the color correction matrix for skin color enhancement based on the data set of the Macbeth color card for skin tone enhancement and the first image through a color correction matrix generation algorithm.

The data processing module is further configured to perform the first interpolation comprising:

$H10 = a1*H0 + a2*H1;$ $S10 = b1*S0 + b2*S1;$ $V10 = c1*V0 + c2*V1;$ wherein, the value ranges of a1, a2, b1, b2, c1, and c2 are all [0,1]; and the second interpolation comprising:

$H20 = a1*H0 + a2*H2;$ $S20 = b1*S0 + b2*S2;$ $V20 = c1*V0 + c2*V2;$ wherein, the value ranges of a1, a2, b1, b2, c1, and c2 are all [0,1].

The data processing module is further configured to: acquire a first target image of a best visual effect taken by the endoscope in a first subject;

calculate a basic tone of the first target image, including the coordinates of a point in a HSV space resulting in the set of color enhancement target data.

The data processing module is further configured to: acquire a second target image taken by a preferred reference endoscope in the first or a second subject;

calculate a basic tone of the second target image, including coordinates of a point in HSV space resulting in the set of color enhancement target data.

The data processing module is further configured to: calculate a weighted average value of pixels of the first target image with wij being a weight of a pixel with coordinates of i and j, and convert the weighted average value to HSV space resulting in the basic tone of the first target image, wherein, wij is determined by:

converting the first target image to HSV space resulting in a first temporary image;

generating a first data set of a two-dimensional histogram of H and S from the first temporary image;

perform a threshold filtering on the first data set to obtain a second data set of the two-dimensional histogram;

acquiring a centroid PCenter of the second data set;

calculating the distance dij from each pixel in the second data set to PCenter, wherein wij and dij are inversely proportional and wij equals 0 for pixels not in the second data set and wij equals 0 for pixels not in the second data set.

The data processing module is further configured to: calculate a weighted average value of pixels of the second target image with wij being a weight of a pixel with coordinates of i and j, and convert the weighted average value to HSV space resulting in the basic tone of the second target image, wherein, wij is determined by:

converting the second target image to HSV space resulting in a first temporary image;

generating a first data set of a two-dimensional histogram of H and S from the first temporary image;

perform a threshold filtering on the first data set to obtain a second data set of the two-dimensional histogram;

acquiring a centroid PCenter of the second data set;

calculating the distance dij from each pixel in the second data set to PCenter, wherein wij and dij are inversely proportional and wij equals 0 for pixels not in the second data set and wij equals 0 for pixels not in the second data set.

An endoscopic image color enhancement method implementable by a software module of a processor of an endoscope or a terminal device connected to an endoscope or having access to endoscopic images such as a display or viewing platform for diagnostic examination, comprises the following steps:

acquiring a set of color enhancement target data, the set of color enhancement target data including coordinates (H0, S0, V0) of a point P0 in HSV space;

obtaining data of color patches of first row and first column of the Macbeth color card, including the coordinates (H1, S1, V1) of a point P1 in HSV space;

obtaining data of the color patches in the first row and second column of the Macbeth color card, including the coordinates (H2, S2, V2) of a point P2 in the HSV space;

performing a first interpolation of the coordinates of P0 and the coordinates of P1, then replacing the coordinates of P1 with the result of the first interpolation, and performing a second interpolation of the coordinates of P0 and the coordinates of P2, and then using the result of the second interpolation to replace the coordinates of P2;

merging data of the rest patches of Macbeth color card with the replaced P1 coordinates and the replaced P2 coordinates resulting in a data set of the Macbeth color card for skin tone enhancement;

generating a color correction matrix for skin color enhancement based on the data set of the Macbeth color card for skin tone enhancement and the first image through a color correction matrix generation algorithm;

performing a color enhancement of an endoscopic image using the color correction matrix.

A brief discussion of the drawings

FIG. 1: Module diagram of the endoscopic image color enhancement system.

Figure 2:
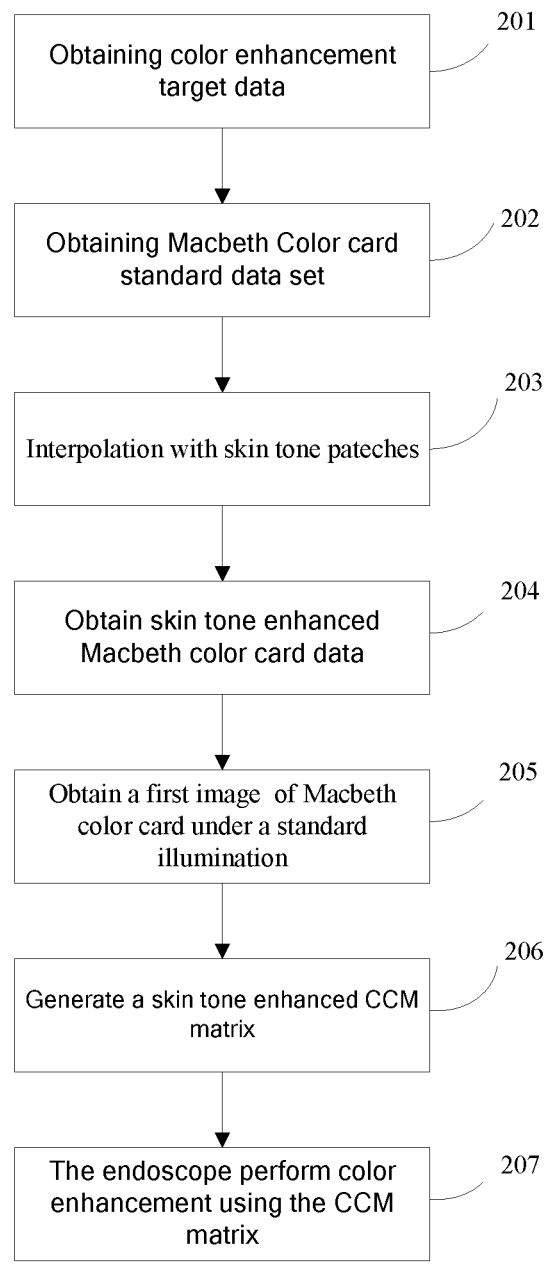

FIG. 2: Flow chart of the process for color enhancement of endoscopic images.

Figure 3:
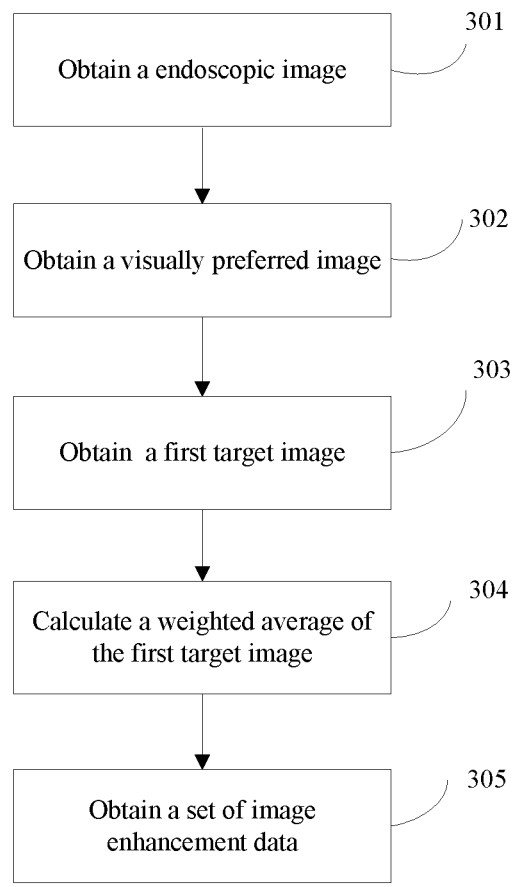
Figure 4:
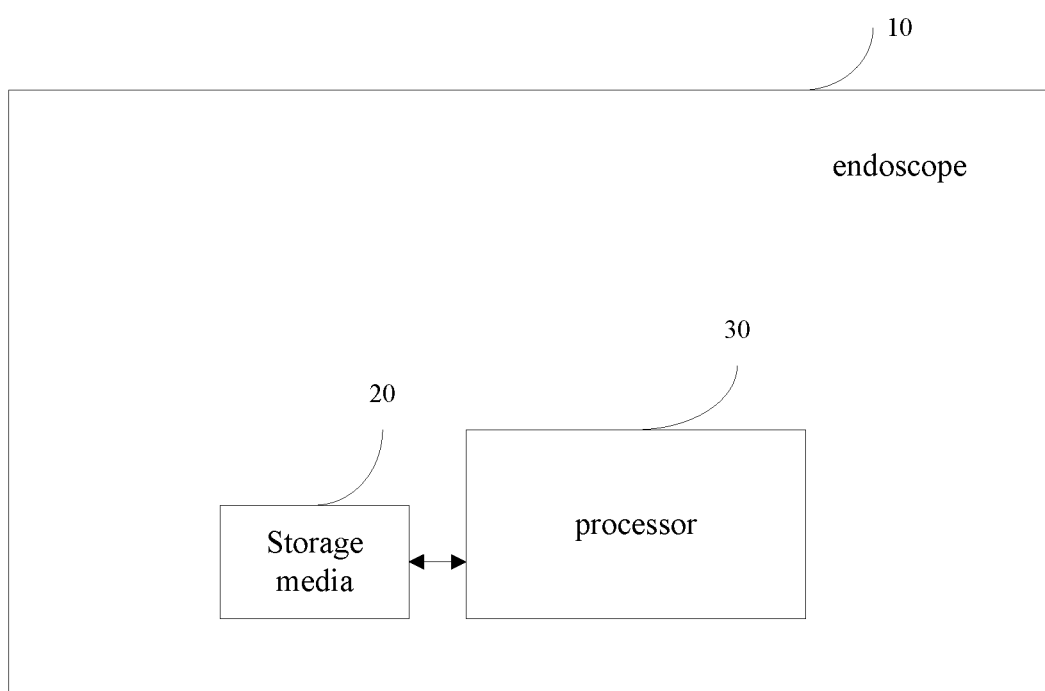

FIG. 3: Flow chart of generating the color enhancement target data;

FIG. 4: An embodiment of an endoscope incorporating the color enhancement functionality

DETAILED DESCRIPTION

An endoscope is preferably equipped with LED light source for illumination, preferably with a color temperature between 3000 and 7000 k. The image color of the endoscope mainly depends on the illumination, the spectral characteristics of the objects in the scene, which is the digestive tract of a patient as relating to the current invention, and the image sensor and processor used to capture the image. The mucous membrane is the main structure of the normal human digestive tract. It is usually reddish and constitutes the base tissue for the basic tone of the endoscopic image. The basic tone or the predominant tone of an endoscopic image can be achieved preferably by calculating a weighted average of image pixels preferably in a sRGB color space, and preferably converting the weighted average from the sRGB space to HSV space. Other tones visible under the endoscope include bluish submucosal veins, food residues, digestive fluids, abnormal diseased tissues, and image noise.

A color correction matrix is a 2D data matrix comprising 3*3 elements. A color correction matrix operates on a pixel of an image typically in a linear R, G, B color space by the following formula:

$$[R',G',B']=A*[R,G,B]^T.  \quad [1]$$

Most imaging devices including the camera module in an endoscopy incorporate a CCM module in the ISP pipeline that operates in real time on every pixel of an image acquired by the image sensor. Data of color correction matrix are loaded to ISP hardware at the initialization and dynamically refreshable. Software based implementation of a color processing of CCM operation is also applicable on various platforms. To acquire a standard color correction matrix, a camera turns off its CCM module, takes a first image of a standard color card preferably the Macbeth color card under a standard illumination, wherein an color correction matrix generation algorithm runs the image and a data set of Macbeth color card to find out a set of optimal data which can performs formula [1] on the first image such that the output image data of the first image match a set of target data of the standard color card patch by patch within an acceptable range of error. There are many ways to implement a color correction matrix generation algorithm in the prior art, and since the objective is not for inventing a novel color correction matrix generation algorithm, there is no need to describe it in detail.

The color patches in the first row, first column and first row and second column of the Macbeth color card are the closest to and represent the human skin tone and are preferably referred to as the skin tone patches hereby. It is a known technique in prior art to generate a color correction matrix for enhancing the skin color by altering the values of the skin tone patches in a color correction matrix generation process. Due to a large amount of data showing that the color pick of the human digestive tract under a preferred endoscope lighting color temperature appears close to skin tone, it suggests enhancing the endoscopic image just like enhancing the skin color in a beauty camera.

As in FIG. 1, the endoscope 101, after turning off the working lighting of the endoscope and CCM function of its ISP, takes a first image of the Macbeth color card under a standard illumination of a color temperature matching the working lighting color temperature of endoscope 101 or another endoscope of the same model including having the same type of image sensor as 101. Preferably, the color temperature of the working lighting of endoscope 101 may be 5000K; further, endoscope 101 adopts a color correction matrix, which is generated by module 102 based on the first image, in the CCM module of the image processor for real-time enhancement of the image captured by endoscope 101; A data processing module 102 is configured to: acquire a set of color enhancement target data preferably including coordinates (H0, S0, V0) of a point P0 in the HSV space; Obtain standard data of the color patches in the first row and the first column of the Macbeth color card, including preferably coordinates (H1, S1, V1) of a point P1 in the HSV space; Obtain standard data of the color patches in the first row and the second column of the Macbeth color card, including preferably coordinates (H2, S2, V2) of a point P2 in the HSV space; perform a first interpolation between the coordinates of P0 and the coordinates of P1, then replaces the coordinates of P1 with the result of the first interpolation; performs a second interpolation between the coordinates of P0 and the coordinates of P2, then replaces the coordinates of P2 with the result of the first interpolation; merge data of the rest patches of standard data of the Macbeth color card color with the replaced P1 coordinates and the replaced P2 coordinates to obtain a data set of the Macbeth color card for skin color enhancement; generate the color correction matrix for skin color enhancement through a color correction matrix generation algorithm using the data set of the Macbeth color card for skin color enhancement and the first image which is adopted preferably by endoscope 101 or another endoscope of the same model as endoscope 101 for endoscopic image enhancement in real time or by a software based color processing platform.

The first interpolation preferably comprises:

$$H10=a1*H0+a2*H1; \quad [2]$$

$$S10=b1*S0+b2*S1; \quad [3]$$

$$V10=c1*V0+c2*V1 \quad [4],$$

wherein, the value of a1, a2, b1, b2, c1, and c2 are in [0,1].

The second interpolation preferably comprises:

$$H20=a1*H0+a2*H2 \quad [5];$$

$$S20=b1*S0+b2*S2 \quad [6];$$

$$V20=c1*V0+c2*V2, \quad [7]$$

wherein, the value of a1, a2, b1, b2, c1, and c2 are in [0,1].

FIG. 3 is a flow chart for obtaining a set of color enhancement target data from an endoscopic image. Step 301 obtains an image by an endoscope in a first subject in a preview mode. Step 302 obtain multiple images in preview mode by adjusting the hue and saturation parameters of the camera of the endoscope. Step 303 captures an image with the best visual effect as a first target image. Step 304 calculate a weighted average value of pixels of the first target image with wij being a weight of a pixel with coordinates of i and j, wherein, wij is determined by: converting the first target image to HSV space resulting in a temporary image; generating a first data set of a two-dimensional histogram of H and S from the temporary image;

performing a threshold filtering on the first data set resulting in a second data set of the two-dimensional histogram;

acquiring a centroid PCenter of the second data set;

calculating the distance dij from each pixel in the second data set to PCenter, wherein wij and dij are inversely proportional and wij equals 0 for pixels not in the second data set. Step 305 generates the set of color enhancement target data by converting the weighted average to the HSV color space.

FIG. 4 is a schematic diagram of an endoscope incorporating the system or method of the endoscopic image color enhancement.

The embodiments described above are for the purpose of illustration, any obvious changes derivative of this disclosure is claimed within the protection scope of the present invention.

The invention claimed is:

1. A method for endoscopic image color enhancement, comprising the following steps:

acquiring a set of color enhancement target data resulting in coordinates of P0;

obtaining data of color patch of first row and first column of Macbeth color card resulting in coordinates of P1;

obtaining data of color patch in the first row and second column of the Macbeth color card resulting in coordinates of P2;

if the difference between the set of color enhancement target data and the data of color patch of the first row and the first column of the Macbeth color card is smaller than a threshold, performing a first interpolation of the coordinates of P0 and the coordinates of P1, then replacing the coordinates of P1 with result of the first interpolation, and performing a second interpolation of the coordinates of P0 and the coordinates of P2, and then using result of the second interpolation to replace the coordinates of P2;

merging data of rest patches of the Macbeth color card with replaced P1 coordinates and replaced P2 coordinates resulting in a data set of the Macbeth color card for skin tone enhancement;

generating a color correction matrix for skin color enhancement based on the data set of the Macbeth color card for skin tone enhancement;

performing a color enhancement of an endoscopic image using the color correction matrix.

2. One or more non-transitory program storage devices, containing instructions readable by one or more processors for causing the one or more processors to perform the method of claim 1.

3. A capsule endoscope, comprising a camera and a processor, wherein the processor is configured to acquire a set of color enhancement target data resulting in coordinates of P0;

obtain data of color patch of first row and first column of Macbeth color card resulting in coordinates of P1;

obtain data of color patch in the first row and second column of the Macbeth color card resulting in coordinates of P2;

if the difference between the set of color enhancement target data and the data of color patch of the first row and the first column of the Macbeth color card is smaller than a threshold, perform a first interpolation of the coordinates of P0 and the coordinates of P1, then replacing the coordinates of P1 with result of the first interpolation, and perform a second interpolation of the coordinates of P0 and the coordinates of P2, and then using result of the second interpolation to replace the coordinates of P2;

merge data of rest patches of the Macbeth color card with replaced P1 coordinates and replaced P2 coordinates resulting in a data set of the Macbeth color card for skin tone enhancement;

generate a color correction matrix for skin color enhancement based on the data set of the Macbeth color card for skin tone enhancement;

and the camera is configured to perform a color enhancement of an endoscopic image using the color correction matrix.

* * * * *